United States Patent [19]

Weissman

[11] 4,368,040
[45] Jan. 11, 1983

[54] DENTAL IMPRESSION TRAY FOR FORMING A DENTAL PROSTHESIS IN SITU

[75] Inventor: Bernard Weissman, New York, N.Y.

[73] Assignee: Ipco Corporation, White Plains, N.Y.

[21] Appl. No.: 269,341

[22] Filed: Jun. 1, 1981

[51] Int. Cl.³ .............................................. A61C 9/00
[52] U.S. Cl. ....................................... 433/36; 433/37; 433/45; 433/223; 433/41
[58] Field of Search ....................... 433/36, 37, 41, 45, 433/46, 47, 213, 214, 215, 217, 223

[56] References Cited

U.S. PATENT DOCUMENTS

| | | | |
|---|---|---|---|
| 508,677 | 11/1893 | Burlingame | 433/47 |
| 1,093,125 | 4/1914 | Guilford | 433/46 |
| 1,094,203 | 4/1914 | Eaton | 433/46 |
| 1,179,317 | 4/1916 | Hurrey | 433/47 |
| 1,561,052 | 11/1925 | Brown | 433/37 |
| 2,685,137 | 8/1954 | Thompson | 433/41 |
| 3,302,289 | 2/1967 | Spaulding | 433/214 |
| 3,878,610 | 4/1975 | Coscina | 433/37 |
| 3,978,585 | 9/1976 | Holcomb | 433/41 |
| 3,987,545 | 10/1976 | Kennedy | 433/36 |
| 4,251,209 | 2/1981 | Bekey et al. | 433/37 |

FOREIGN PATENT DOCUMENTS 837283  4/1952  Fed. Rep. of Germany ........ 433/47

Primary Examiner—Gene Mancene
Assistant Examiner—John J. Wilson
Attorney, Agent, or Firm—Goodman & Teitelbaum

[57] ABSTRACT

A dental impression tray for forming a negative impression of a dental area to be restored. Application devices on the tray permit injection of dental restorative material into a mold cavity defined between the negative impression formed in the tray and the dental area after preparation thereof for restoration. In this manner, a dental prosthesis can be formed in situ utilizing the dental impression tray itself as part of the mold forming device. In a modified form, the tray can be separated into two half sections, whereby in further embodiments thereof, the half sections can be joined together and are interchangeable with half sections of different sizes.

21 Claims, 18 Drawing Figures

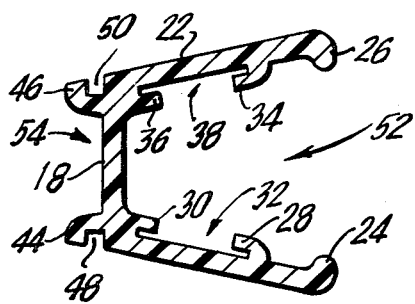
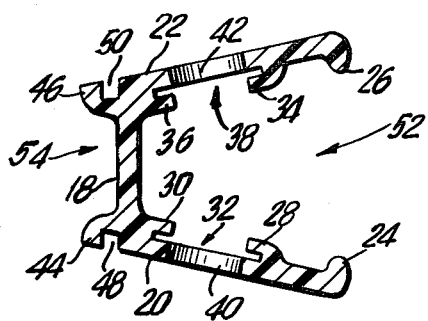
FIG.4  FIG.5
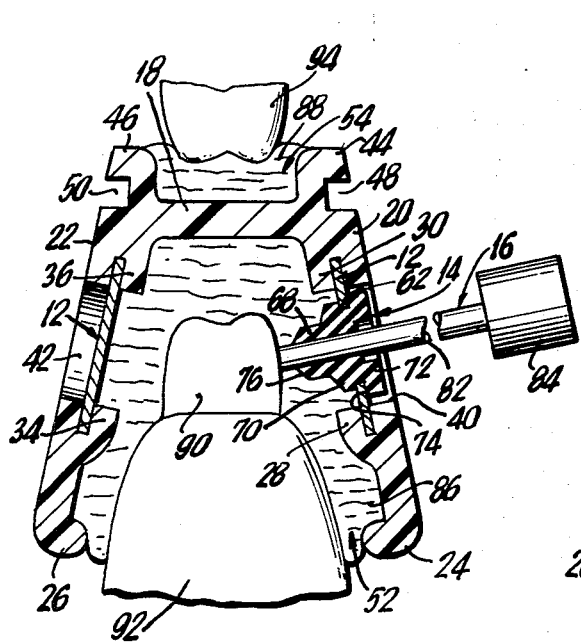
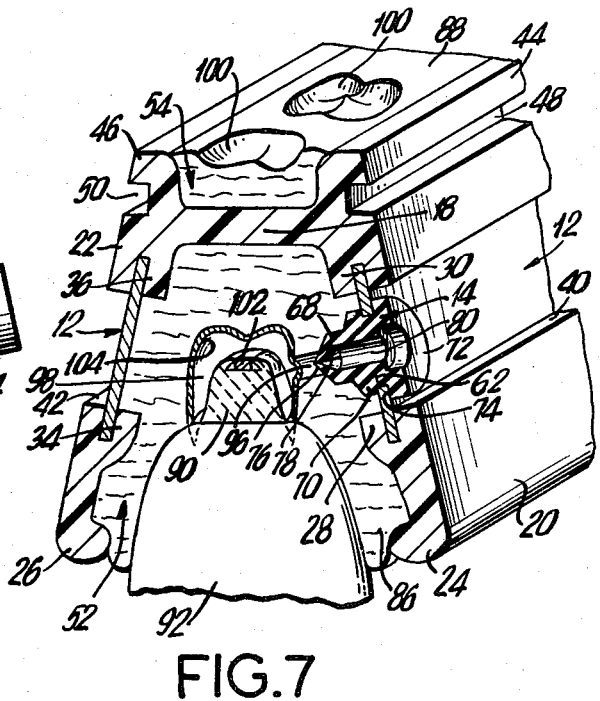
FIG.6A  FIG.7
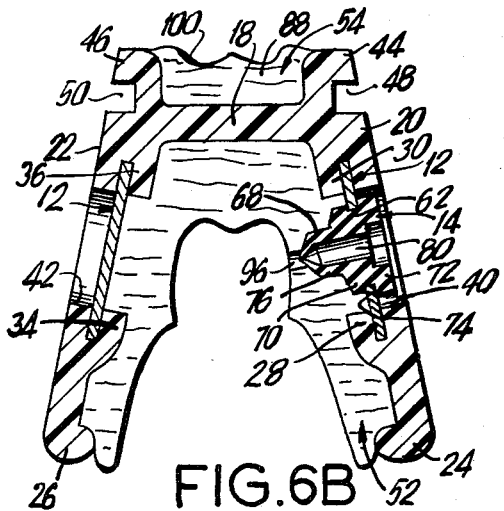
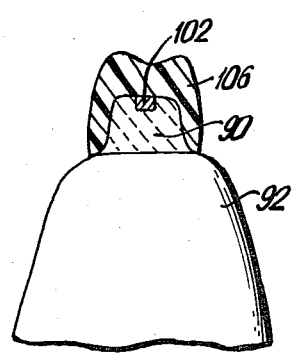
FIG.6B  FIG.8

DENTAL IMPRESSION TRAY FOR FORMING A DENTAL PROSTHESIS IN SITU

BACKGROUND OF THE INVENTION

This invention relates to dental impression trays, and more particularly for a method and apparatus for molding a dental prosthesis in situ, and also the dental impression trays which can be separated and which can have interchangeable parts.

In repairing dental areas, it is frequently necessary to form a temporary prosthesis for the restoration of defective teeth in a patient's mouth prior to forming the permanent prosthesis. The methods previously used first require the formation of a negative impression in a patient's mouth prior to the preparation of the teeth for receiving the prosthesis. Typically, a positive mold of the teeth is then formed. The teeth are then prepared to receive the prosthesis by cutting them down as is necessary. A second positive mold is then formed of the prepared teeth. Sections of the first positive mold are then cut and properly trimmed and cut down so as to suitably fit in the second positive mold and thereby form the necessary prosthesis on the mold. The necessary dental restorative material is then utilized to form a prosthesis from the positive mold sections. The prosthesis is then replaced in the mouth.

As an improvement over this method, it has been suggested to make a dental prosthesis in situ. In U.S. Pat. No. 3,987,545 there is disclosed the method of forming such a dental prosthesis in situ by first preparing a negative impression of the patient's mouth and from that impression, forming a positive model of the area where tooth restoration is required. An elastomeric mold half is then formed over such positive model. The mold half is formed with overlapping boundaries of the tooth area to be stored in all directions by a predetermined distance. The patient's teeth are then prepared for the restoration including cutting down of selected teeth. The elastomeric mold half is then placed back onto the patient's mouth over the tooth areas prepared for restoration. A vacuum is then caused in the mold cavity formed between the elastomeric mold half and the tooth area, and after the vacuum is achieved, suitable dental restorative material is sent into such mold cavity to form the dental prosthesis in situ.

In order to avoid the necessity of working directly in the patient's mouth, U.S. Pat. No. 4,080,736 provides an additional variation whereby a hard model of the tooth area is formed after it has been prepared for restoration. The previously formed elastomeric mold half is then placed over the hard model outside of the patient's mouth and secured together to form a mold cavity therebetween. The assembly is then placed in a vacuum chamber and suitable dental restorative material is then flowed into the mold cavity to form the dental prosthesis. The prosthesis is then placed into the patient's mouth.

While the formation of the dental prosthesis in situ has been attemped, the various methods and apparatus utilized required numerous steps which caused excessive time and effort until such prosthesis was formed. In all cases, it was first necessary to convert the negative impression of the dental area into a positive model and from the positive model make an elastomeric mold which could then be utilized for the formation of the prosthesis in situ. This procedure itself, in addition to being time consuming, also facilitated errors so that the dental prosthesis formed might not be perfectly fitted and might cause discomfort and injury to the patient.

An additional problem is that the formation of the negative impression utilized a dental impression tray. However, the dental impression tray must be varied in accordance with the sections and configurations of the dental areas. For example, the upper and lower arches of the mouth may vary, and the left and right portions may differ in size. Thus, depending upon the type of impression needed, the depth of the impression tray required will also vary.

When utilizing a standard dental impression tray, it becomes difficult to form the negative dental impression in the portions of the mouth to be restored. Excessive dental impression material is required when utilizing a standard tray for only small areas. Furthermore, in many cases, visability of the area to be restored becomes blocked by means of the large dental impression tray when it is not suitably restricted for the particular area to be restored.

Accordingly, there is need for improvement in the formation of a dental prosthesis in situ. There is also a need for a suitable dental impression tray which can be varied so as to permit modification of the tray for specific utilization in connection with particular sections and configurations of the dental area to be restored.

SUMMARY OF THE INVENTION

Accordingly, it is an object of the present invention to provide an improved method and apparatus for making a dental prosthesis in situ, the dental prosthesis preferably being of the temporary type.

Another object of the present invention is to provide a dental impression tray which can be utilized in connection with the formation of a dental prosthesis in situ.

Still another object of the present invention is to provide an improved dental impression tray which permits utilization of the tray itself in the formation of a mold cavity for forming a dental prosthesis in situ.

Yet another object of the present invention is to provide a method for utilizing a dental impression tray in the direct formation of a dental prosthesis in situ.

A further object of the present invention is to provide a dental impression tray which can be separated into sections so as to permit interchangeability of tray sections, thereby permitting the joining together of various tray sections to conform with the particular dental area to be restored.

Still another object of the present invention is to provide a dental impression tray which can be separated into two mating halves so as to utilize only one half of the tray for specific areas of dental work.

Another object of the present invention is to provide a dental impression tray holder which can be utilized in conjunction with various tray sizes, and permiting interchangeability of sizes and styles of trays to conform with particular configurations of a dental area to be restored.

Briefly, in accordance with the present invention, there is provided a dental impression tray for forming therein a negative impression of a dental area to be restored. Casting apparatus is provided on the tray for application of dental restorative material into a mold cavity defined between the negative impression in the tray and the dental area after preparation thereof for restoration, so as to form the dental prosthesis in situ, the dental prosthesis preferably being of the temporary type.

In an embodiment of the invention, the casting apparatus includes openings formed in the tray so as to accommodate a valve which can be positioned adjacent to the dental area to be restored. A removable plug is insertable into a central bore of the valve so as to extend up to the dental area to be restored and to define in the negative impression a sprue channel for use during the application of the dental restorative material.

The valve is disposed through the tray opening and is held in place by means of a strap insertable in a channel provided on the inside of a side wall of the tray, the strap having an opening therein to retain the valve in place.

The invention also comprises a method for forming the dental prosthesis in situ. The method includes the steps of forming, in a dental impression tray, a negative impression of a dental area to be restored. The dental impression tray is removed, and tooth preparatory work is then carried out in the dental area, including the removal of portions thereof. The dental impression tray is then reset on the dental area so as to form a mold cavity between the negative impression formed in the tray and the prepared dental area. Dental restorative material is then injected into the mold cavity so as to form the dental prosthesis in situ. The dental impression tray is then removed leaving the prosthesis suitably fixed in place in the mouth.

The invention also contemplates the formation of a dental impression tray for forming a negative impression of a dental area, wherein the tray includes a substantially arcuate portion having a base wall and upstanding side walls so as to define a trough-like configuration. An elongated handle is provided for supporting the arcuate portions. Separating means are included so as to separate the arcuate portion into arcuate half-sections thereby selectively facilitating varied usage of the tray assembly for different mouth configurations, whereby sections of the tray, in some embodiments of the present invention, are interchangeable.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which:

FIG. 4 is a cross sectional view of the tray taken along line 4—4 of FIG. 3;

FIG. 5 is a cross sectional view of the tray taken along line 5—5 of FIG. 3;

FIG. 6A is a cross sectional elevational view of a step in utilization of the dental impression tray in accordance with the method of the present invention, showing the tray positioned in the patient's mouth;

FIG. 6B is a cross sectional elevational view similar to FIG. 6A, showing the tray removed from the patient's mouth;

FIG. 7 is a perspective view, in cross section, similar to that shown in FIGS. 6A and 6B, of a subsequent step in the formation of the dental prosthesis, showing the tray repositioned in the patient's mouth;

FIG. 8 is a cross sectional elevational view showing the dental prosthesis in place after its formation in situ, in accordance with the present invention;

In the various figures of the drawing, like reference characters designate like parts.

DETAILED DESCRIPTION OF THE PREFERRED EMBODIMENT

Figure 1:
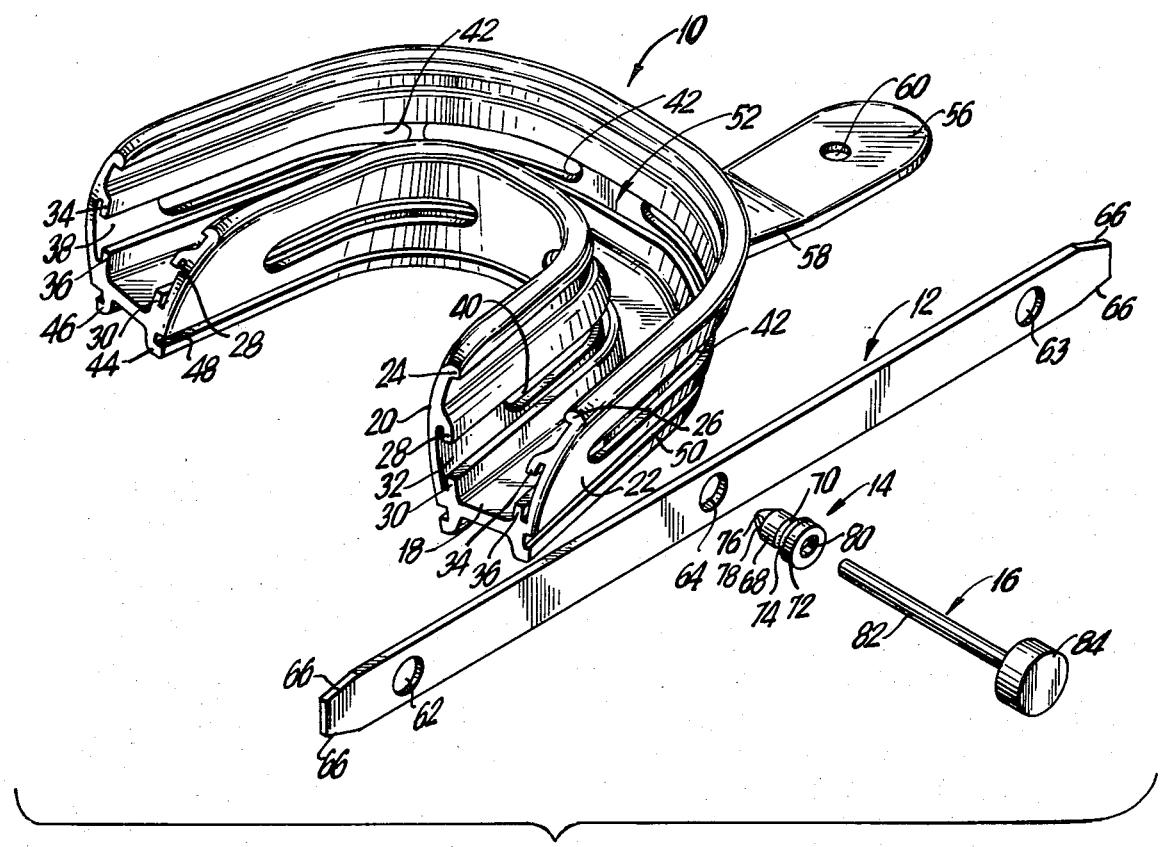
FIG. 1 is a perspective exploded view of the various parts of the dental impression tray assembly in accordance with the present invention.
Figure 2:
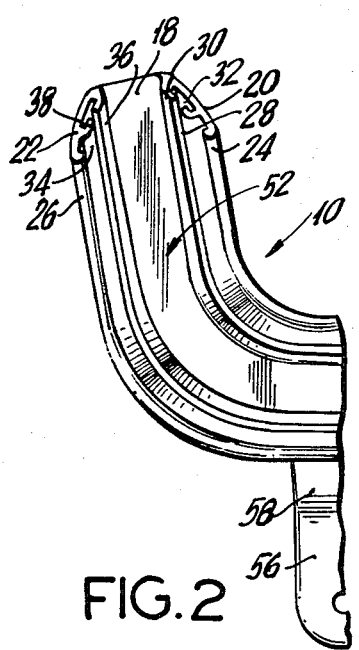
FIG. 2 is a partial plan view of the dental impression tray shown in FIG. 1.
Figure 3:
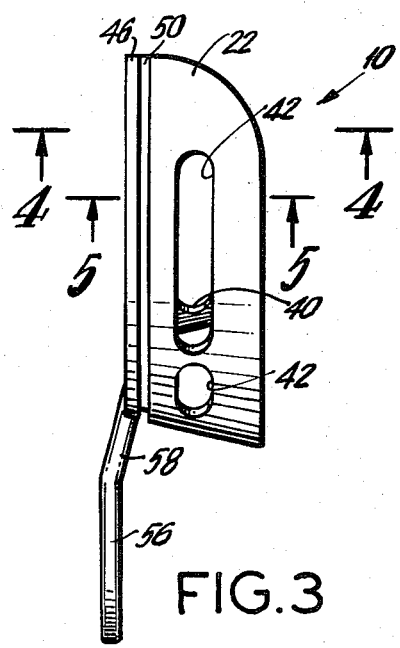
FIG. 3 is a side view of the dental impression tray shown in FIGS. 1 and 2.

Referring now to FIGS. 1-5, the dental impression tray assembly is shown to include a dental impression tray 10, an elongated strap 12, a one-way valve 14, and a sprue former 16.

The dental impression tray 10 is formed in an arcuate or substantially U-shape and includes a base wall 18 with a pair of upstanding side walls 20 and 22. The side walls 20, 22 together with the base wall 18 form a trough-like configuration which is substantially U-shaped in cross section. The side walls 20, 22 are upwardly flared so as to permit easier utilization. The upper ends of the side walls 20, 22 are inwardly bent to form the lips 24, 26.

On the inside of the side wall 20 there is formed a pair of opposing finger-like wall sections 28, 30 linearly extending along the entire inner periphery of the side wall. The wall sections 28, 30 face each other forming approaching arms which define therebetween a channel 32 having an open mouth. A similar arrangement on the inside of the side wall 22 includes wall sections 34 and 36 which define the open channel 38. It should be noted that a passageway is formed by the channels 32 and 38 which can receive the strap 12 so as to respectively position the strap adjacent to the interior surfaces of the side walls 20, 22.

Elongated locating slots 40 are positioned longitudinally along the side wall 20 and similar elongated locating slots 42 are positioned along the side wall 22. It should be noted that the slots 40, 42 are respectively coaligned with the channels 32, 38.

Extending from the opposing side of the base wall 18 are upstanding side walls 44, 46 which are shorter than the corresponding side walls 20, 22. A linear keyway 48 is formed around the side wall 44 and a corresponding keyway 50 is formed linearly around the side wall 46. The keyways are provided for facilitating manipulation of the tray including setting and removal of the tray from dental areas within the mouth.

The base wall 18 together with the upstanding side walls 20, 22 define a trough area 52 which can receive dental impression material of a type well known in the formation of negative impressions of the dental area within the mouth. On the opposing side, the base wall 18 together with the side walls 44 and 46 define a shallower well area 54 which also receives dental restorative material.

Laterally extending from the rear of the dental impression tray 10 is a handle 56 integrally formed with and extending from the base wall 18 of the tray. The handle 56 includes a thicker portion 58 adjacent the tray and a thinner portion at the distal end thereof for facilitating grasping of the tray. An aperture 60 is formed in the handle for facilitating hanging of the dental impression tray for drying and storage. However, it should be noted, that the handle could be a removable type handle, as shown for example in FIG. 15, as will be set forth below, whereby in some dental procedures, a handle may not be required.

The strap 12 is formed of flat flexible material, such as stainless steel, and includes spaced apart transverse openings 62, 63 and 64. The distal edges of the strap are tapered at 66 to facilitate insertion of the strap 12 within the channels 32, 38 provided on the interior of the side walls 20, 22. One strap 12 is positioned in each channel 32, 38, or the strap 12 can be cut into two portions so that one strap portion is positioned in a respective one of the channels 32, 38. The thickness of the strap is such as to be able to be received in the passageway provided between each of the wall sections 28, 30 and 32, 34 defining the channels so as to abut the inner surfaces of the side walls of the tray when inserted in the channels.

The strap 12 can be adjustably slid through either one of the channels about the periphery of the side walls so as to suitably position any one or all of the transverse openings 62, 63, 64 in a position adjacent to the dental area to be restored. It should be appreciated that at least one or more of the transverse openings 62, 63, 64 of one strap or strap portion will be aligned with the selected one of the elongated locating slots 40, 42 in the respective side wall 20 or 22 of the tray, depending upon the dentist's access thereto, so that when this one strap is positioned, at least one or more of the transverse openings 62, 63, 64 in this one strap will provide a through passage from the tray exterior to the interior of the dental tray, thus gaining access to the dental area to be restored from outside of the dental tray. The other strap or strap portion is positioned in the other channel so that the transverse openings 62, 63, 64 are not aligned with any of the non-selected elongated locating slots 40 or 42, thus blocking the access therethrough. Accordingly, to facilitate this blocking arrangement, the end portions of the other strap containing the transverse openings 62 and 63 can be cut off.

Valve 14 includes a central shank portion 68 with an enlarged shoulder portion 70 and a further enlarged head portion 72. An annular peripheral groove 74 is formed about the valve proximate the junction between the shoulder portion 70 and the head portion 72. The forward end of the valve includes a tapered frustroconical tip 76 having a slit 78 formed therein to permit resilient opening and closing of the tip end. A bore 80 is formed entirely through the valve. The valve acts as a one-way valve, only permitting entry therethrough in the direction from the head portion 72 to the tip 76.

The sprue former 16 includes a longitudinal shaft portion 82 and a head portion 84 at one end thereof. The shaft 82 is sized so as to fit within the central bore 80 of the valve 14.

Referring now to FIGS. 6A, 6B and 7, utilization of the dental impression tray will now be described. Initially, two straps 12 are suitably placed respectively within the channels 32, 38 on the interior wall 20 and the exterior wall 22 of the dental impression tray. One of the straps is positioned so as to locate a selected one of transverse openings 62, 63 or 64 adjacent to the dental area to be restored. The valve 14 is then inserted through that transverse opening, such as opening 62 as shown, so that the strap is engaged in the valve groove 74. It should be noted that the valve 14 also passes through the associated elongated locating slot, such as slot 40 as shown, and through the mouth of the channel 32 so as to extend into the interior of the dental tray within the trough area 52. The sprue formed 16 is then inserted through the central bore 80 of the valve 14.

If required, more than one valve 14 can be positioned in the tray for association with additional dental areas within the patient's mouth. It is noted, that the straps 12 close off the remaining elongated locating slots 40, 42 so that the transverse openings 62, 63 and 64 are not in alignment therewith, as shown in the drawings.

Suitable dental impression material 86, such as silicone rubber, hydrocolloid and the like, is placed within the trough area 52 defined on one side of the base wall 18, and additional dental impression material 88 is formed in the well area 54 defined on the opposing side of the base wall 18. The dental impression tray is then placed in the patient's mouth over the dental area to be restored prior to any preparatory work being done on the dental area. The tray 10 is placed over the specific teeth, such as tooth 90, to be restored and extends downward to cover the gum area 92 beneath the tooth or teeth. The sprue former 16 is extended so that it abuts the edge of the tooth 90, as shown in FIG. 6A. A negative impression of the dental area to be restored is then formed within the dental impression material 86, and the sprue former 16 is removed as shown in FIG. 6B.

It should be noted, that simultaneously with the formation of the negative impression of the dental area to be restored, there is also formed a negative impression in the well area 54 within the impression material 88 by means of the tooth 94 which represents the teeth opposite the dental area to be restored. As a result, a shallow negative impression of the opposing teeth will be formed in the opposing side of the dental tray. This opposing negative impression will be subsequently utilized for facilitating the repositioning of the tray in the mouth area, as set forth below.

After the negative impressions are formed in the impression tray, the dental impression tray is removed from the mouth area, as shown in FIG. 6B, and is set aside to permit the material to harden, as is well known in the art.

The tooth area to be restored is then suitably prepared to receive the dental prosthesis. Typically, such preparation includes cutting down of a tooth to remove the portion that has been damaged or deficient, and properly preparing any adjacent teeth in accordance with well known dental requirements.

After the dental area has been suitably prepared, the dental impression tray is then repositioned in the mouth, as shown in FIG. 7. As noted above, the sprue former 16 has been removed, thus closing the valve 14. At the same time, after removal of the sprue former, a sprue channel 96 remains in the negative impression formed in the impression material 86.

The repositioning or reseating of the dental impression tray is facilitated by means of the shallow impressions 100 of the opposing teeth formed in the impression material 88. It should be noted, as shown in FIG. 7, that the dental area to be restored, including the tooth 90, has been suitably cut down so that a void or space 98 now exists between the stump of the tooth 90 and the negative impression formed in the impression material 86. This void 98 effectively forms a mold cavity in which the dental prosthesis can be formed in situ. The valve 14 is now utilized as an injection valve through which suitable dental restorative material can be injected into the mold cavity 98 formed between the cut down tooth 90 and the negative impression in the tray. Such dental restorative material can typically include acrylic resin material, or other types of restorative material which are suitable for a temporary prosthesis, these materials being well known in the art. The acrylic restorative material is injected through the one way valve 14 and fills the mold cavity 98 to form the dental prosthesis directly in situ.

If desired, a splint 102 can be placed on top of, or inserted within a channel formed in the stump of the dental tooth 90 prior to formation of the dental prosthesis. When the dental restorative material fills the mold cavity 98, the splint 102 will be cast within the dental prosthesis so as to provide additional support for the tooth area being restored.

Additionally, on the surface of the negative impression, suitable coloring material 104 can be placed prior to the repositioning of the dental impression tray on the dental area to be restored. The coloring material 104 matches the actual color tones and hues of the tooth area being restored. When the restorative material is then injected in the the mold cavity 98, the coloring material 104 will be dispersed into the surface of the restorative material so that the coloring material will provide the outer color tone of the dental prosthesis, realistically matching the other natural teeth in the dental tooth area.

After the completion of the dental prosthesis, the dental impression tray can be removed leaving the dental prosthesis suitably in place, the dental prosthesis preferably being of the temporary type. As shown in FIG. 8, after removal of the dental impression tray, and suitably grinding down the sprue, there remains the dental prosthesis 106 formed on top of the tooth stump 90. The splint 102 is secured within the dental prosthesis, and functions as a supportive structure. This temporary dental prosthesis is thus accurately formed, and will avoid the necessity of the complex prior art requirements of forming numerous positives, negatives, numerous molds, and the possibility of inaccuracies being introduced through all the complexity of these prior art steps. The permanent dental prosthesis is fabricated in the conventional manner, and will replace the temporary dental prosthesis of the present invention in due course, as is well known in the dental art.

The dental impression tray that is frequently utilized in connection with dental restoration is a substantially U-shaped configuration, and accordingly includes a substantially complete arcuate semi-circular section conforming to the arcuate shape of the entire upper or lower teeth formation. However, in certain situations, a dental impression need not be made of the complete upper or lower teeth formation, whereby just a portion of the upper or lower teeth requires a dental impression. As a result, utilizing the semi-circular impression trays of the prior art, there is substantial waste of dental impression material. Furthermore, since the impression tray covers more than just the desired area, it frequently blocks visability and prevents accurate positioning of the tray in order to make an impression of the dental area to be restored. Thus, trays having an arcuate 90° section are provided in the dental art, whereby the above described tray of the present invention can also have an arcuate 90° section, as set forth below.

Accordingly, it is desirable to have a dental impression tray which can be utilized for either a complete upper or lower set of teeth, and which can also be modified so as to conform to only a partial mouth area in order to save dental impression material and reduce the difficulty and complexity of making the impression, such dental impression trays being set forth below.

Figure 9:
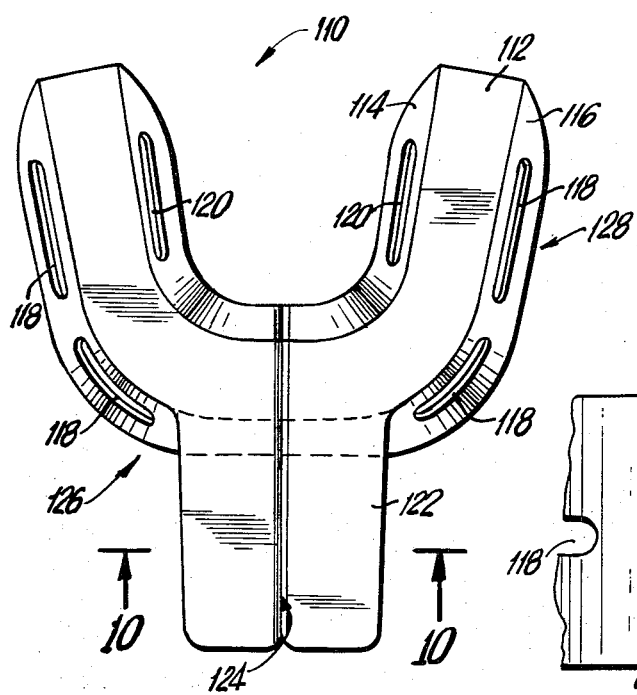
FIG. 9 is a bottom view of a dental impression tray in accordance with another embodiment of the present invention, showing the structure for separating the tray into various sections.
Figure 10:
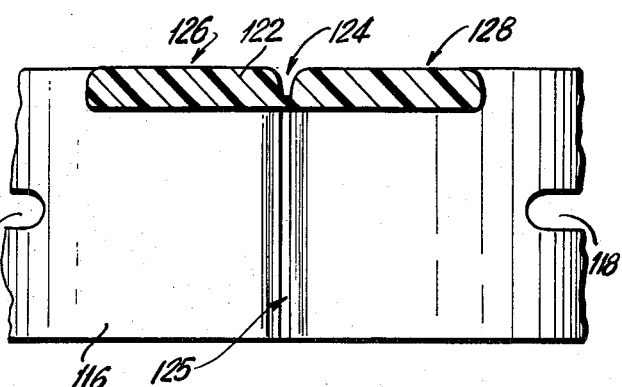
FIG. 10 is a cross sectional view taken along line 10—10 of FIG. 9.

Referring to FIG. 9, there is shown an improved dental impression tray 110 of the aforedescribed type which includes a base or bottom wall 112 and side walls 114, 116. As heretofore described, elongated locating slots 118, 120 are formed in the side walls. Integrally formed with the bottom wall 112 is a handle 122 which extends rearwardly from the tray. The tray 110 is shaped in a substantially U-shaped configuration to provide a substantially semi-circular shape to conform to an entire upper or lower set of teeth. However, extending through the center of the entire tray so as to divide it into two opposing half sections, is a first groove to provide a reduced thickness portion 124, and a second groove in the center of the side wall 116 to provide an associated reduced thickness portion 125, as shown in FIG. 10. The portions 124 and 125 are frangible so that the entire tray can be split in half, so that two sections 126, 128 are separated from each other. In this manner, the option is provided that the tray 110 can be utilized in its entirety to cover a complete upper or lower set of teeth, or the tray 110 can be separated with ease into two halves 126, 128 in order to utilize one half section to cover only that portion of the dental area which requires a negative impression.

Figure 11:
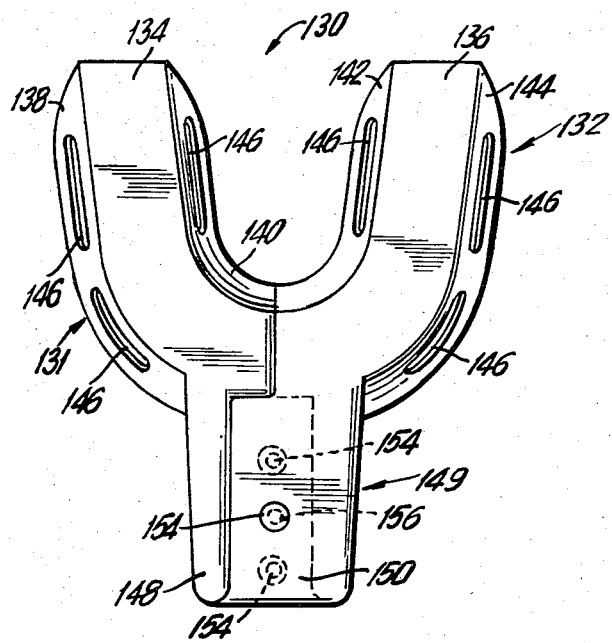
FIG. 11 is a bottom view of another embodiment in accordance with the present invention, showing another structure for separating the impression tray into sections.
Figure 12:
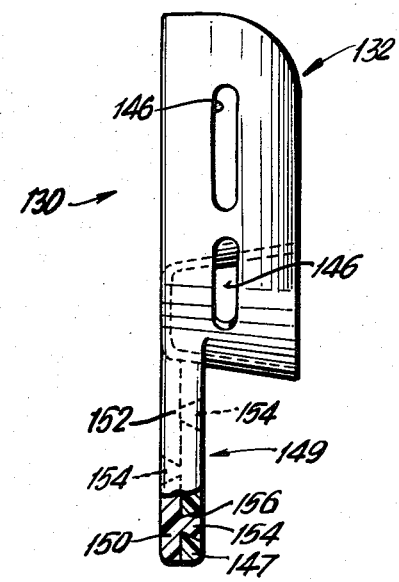
FIG. 12 is side elevational view, partly in cross section, of the embodiment shown in FIG. 11.
Figure 13:
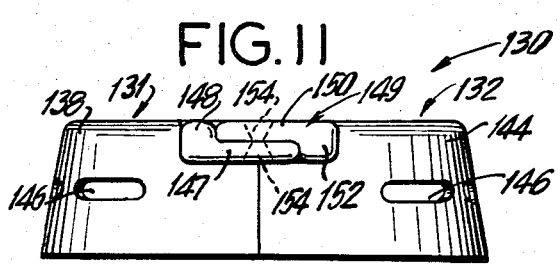
FIG. 13 is a rear elevational view of the embodiment shown in FIG. 11.

Referring now to FIGS. 11-13, another embodiment is shown for separating the trays into two sections. In this embodiment, the tray 130 is actually initially formed in two half sections 131, 132. Each half section includes a respective base wall 134, 136 and respective upstanding side walls 138, 140 on the section 131 and upstanding side walls 142 and 144 on the section 132. Elongated locating slots 146 are provided in the side walls, as heretofore described in connection with FIG. 1.

A handle 149 extends from each base wall 134, 136 to hold the half section. Each handle has a substantially L-shaped cross sectional configuration, as best indicated in FIG. 13. Extending from the base wall 134 of the section 131, the handle includes a laterally flat section 147, and a perpendicular arm section 148 extending from the edge thereof. The handle extending from the base wall 136 of the section 132 includes the flat section 150 which lies in a plane substantially parallel to the plane in which the flat section 147 lies, however, is slightly displaced therefrom. From the opposing side thereof, there is again a perpendicular arm section 152 which extends from the edge thereof.

As shown in FIG. 13, the two handles 149 nestingly fit within each other with the two flat sections 147, 150 overlying each other in a lap joint arrangement, and the two arm sections 148, 152 forming the lateral side edges of the handle assembly.

In order to retain the two sections in place, protrusions 154 extend outwardly from the flat sections 147, 150 and fit into corresponding detents or recesses 156 provided in the opposing flat sections, as best shown in FIG. 12, wherein section 147 has one protrusion 154 and section 150 has two protrusions 154 thereon. This permits snapping the two flat sections 147, 150 together to retain the lap joint arrangement in place. It should be understood that the arrangement of the protrusions and the detents can be reversed. Additionally, other types of locking arrangements can be maintained. Preferably, the protrusions 154 are tapered outwardly from the flat section to provide an enlarged head thereon, wherein the associated recesses 156 have a corresponding configuration to lockingly receive the protrusions 154 therein.

Utilizing the embodiments shown in FIGS. 11–13, the two arcuate sections 131, 132 can be joined to form a complete impression tray 130 in order to cover an entire upper or lower mouth section, when such is needed. At the same time, the two sections 131, 132 can be easily separated to form the two half sections when only a portion of the dental area requires a dental impression.

Figure 14:
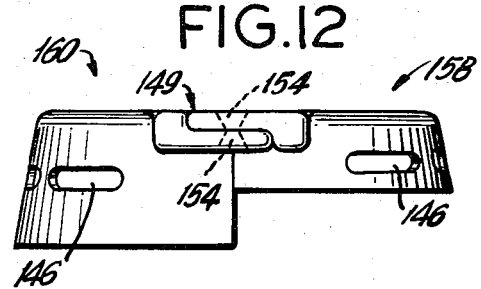
FIG. 14 is a rear view similar to that shown in FIG. 13, wherein one section of the impression tray is shallower than the other section.

Additionally, the tray sections shown in FIG. 14 are similar to the above tray sections 131, 132, however one of the sections 158 is shown to include side walls which are shallower or lower than the side walls of adjacent section 160. This type of tray is useful when an occlusal impression is required and only a shallow depth is needed. Accordingly, not only can the two sections be utilized separate or connected, but the depth of the impression tray of each half section can be modified to accommodate the particular arrangement needed for the dental area whose impression is to be taken.

Figure 15:
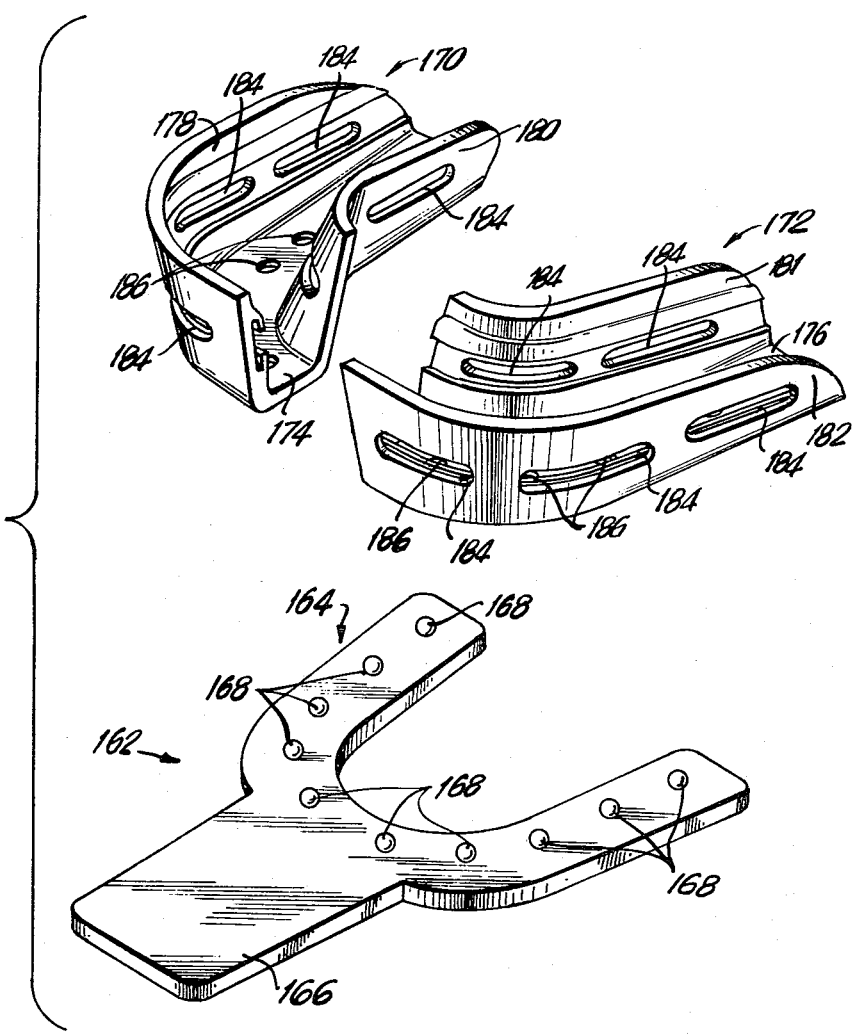
FIG. 15 is a perspective exploded view of another embodiment of the dental impression tray, showing the separation of the tray into various sections.
Figure 16:
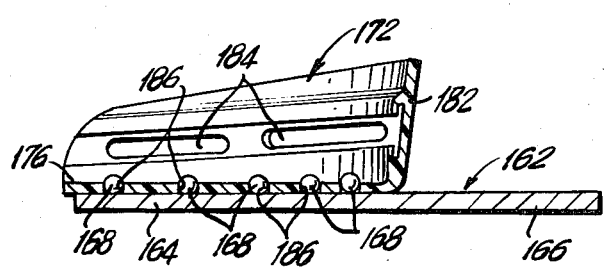
FIG. 16 is a cross sectional elevational view of the tray embodiment shown in FIG. 15.

Referring now to FIGS. 15 and 16, a further arrangement facilitating the separating of the sections is shown. In this embodiment, there is provided a permanent tray holder 162 shown as a substantially flat plate formed in the shape of a yoke arrangement including a substantially U-shaped arcuate section 164 and a rearwardly extending handle section 166. On the arcuate section 164, there is provided spaced apart protrusions 168 outwardly extending from the surface of the tray holder 162.

Supported on the tray holder are two impression tray half sections 170, 172. Each tray half section includes a respective base wall 174, 176. The upstanding side walls 178, 180 are provided from the base wall 174 and corresponding upstanding side walls 181, 182 extend from the base wall 176. As heretofore explained, elongated slots 184 and associated channel forming flanges are provided in all of the side walls.

Detents 186 are provided in each of the base walls 174 and 176 at correspondingly spaced apart positions so as to receive and mate with the associated protrusions 168. In this manner, each of the sections 170, 172 can selectively be snapped onto the permanent tray holder 162 as needed. When an entire upper or lower mouth area requires a dental impression to be made, both half sections will be snapped in place. On the other hand, when only one quadrant of the mouth is required for a dental impression, only one of the sections can be snapped into place.

Figures 17, 18:
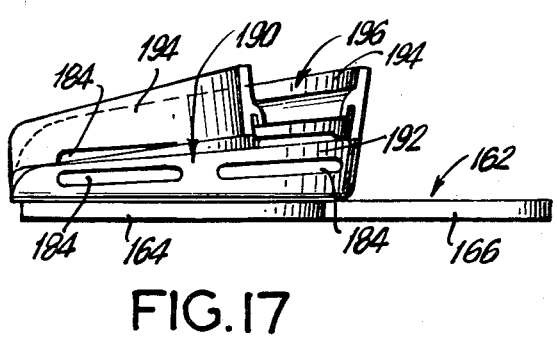
FIG. 17 is a side elevational view of an embodiment similar to that shown in FIG. 15, wherein one section of the tray is shallower than the other section.
FIG. 18 is a rear elevational view of the tray embodiment shown in FIG. 17.

As shown in FIG. 15, the two half sections 170, 172 have upstanding walls of substantially the same height. However, when one mouth quadrant requires a shallow impression tray, as for example in connection with making an occlusal impression of the teeth, the embodiment shown in FIGS. 17 and 18 can be utilized. As indicated, one of the half sections 190 is shown having upstanding walls 192 which are shorter than the upstanding walls 194 of the other section 196. As a result, the section 190 forms a shallower tray than does the section 196. In both cases, the sections are snapped onto the tray holder 162 which thereby supports the two sections. It should be understood that the two sections are provided in modified form so as to make the left hand section the shallower tray, as is required.

With the various combination heretofore described, it is possible to interchange sections of the trays in order to provide various sizes and styles. For example, four different trays can be made available in the four basic sizes that reflect different dental arch sizes. Two trays can be made available for the upper and lower arches, and by using the half tray system, left and right versions of the trays can be provided. In addition, two different heights of trays can be included wherein one has the standard full depth and a companion set is provided with a shallow depth when only an occlusal impression is required. As a result, a total of about 32 different sizes and styles can be made available utilizing the system of the present invention.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A dental impression tray for forming therein a negative impression of a dental area, said tray comprising:

a trough for receiving dental impression material therein;

means on said tray for application of dental restorative material into a mold cavity defined between the negative impression, formed in said trough of said tray, and the dental area after preparation thereof for restoration, so as to form a dental prosthesis, said application means including openings provided in said tray;

valve means insertable in said openings for positioning adjacent to the dental area;

control means for closing said valve means during formation of the negative impression and for opening said valve means for application of the dental restorative material therethrough;

said tray including a base wall and upstanding side walls extending outwardly from one side of said base wall to define said trough, a retaining channel provided along at least one of said side walls, at least one elongated slot provided in said one side wall within said channel; and a strap member adjustably slidable in said channel to abut said one side wall, and at least one transverse opening provided through said strap member for alignment with said slot, said transverse opening receiving said valve means and positioning it within said slot.

2. A dental impression tray as in claim 1, wherein said valve means is a one way valve having a central bore therethrough, and wherein said control means includes a removable plug insertable into said central bore of said valve and extendable to engage the dental area so as to define a sprue channel in the negative impression for use during the application of the dental restorative material.

3. A dental impression tray as in claim 1, wherein said strap member is flexible so as to fit around said one side wall of said tray.

4. A dental impression tray as in claim 1, wherein said tray includes a second set of upstanding side walls extending outwardly from an opposing side of said base wall to define a well for receiving dental impression material in which a second negative impression can be made of another dental area opposing the first mentioned dental area, so as to facilitate repositioning of said tray during application of the dental restorative material.

5. A dental impression tray as in claim 4, wherein said second set of side walls on said opposing side includes a linear keyway in outer surfaces thereof for facilitating manipulation of said tray.

6. A dental impression tray as in claim 1, wherein a pair of spaced apart finger members linearly extend interiorly along said one side wall and face each other so as to define said channel therebetween, said channel being interiorly open to permit passage of said valve means therethrough.

7. A dental impression tray as in claim 1, wherein said valve means includes a shank portion, an enlarged head portion at one end of said shank portion, a resilient tapered tip portion at an opposite end of said shank portion, an annular groove in said head portion to snap fit into said transverse opening of said strap member, and a slit provided in said tip portion to permit one way opening thereof.

8. A dental impression tray as in claim 1, wherein said tray trough is substantially arcuately shaped defined by said base wall and substantially concentric upstanding peripheral side walls of said tray, an elongated integral handle rearwardly extending from said base wall, and reduced thickness portion means longitudinally extending along said handle and transversely extending along said base wall and said side walls for separation of said tray into two opposing sections.

9. A dental impression tray as in claim 1, wherein said tray includes two opposing arcuate half sections, each section having a base wall and upstanding side walls to define said trough, an integral elongated handle extending from each of the base walls, and coupling means for matingly joining said half sections to provide a unitary arcuate tray.

10. A dental impression tray as in claim 9, wherein each of said handles has a substantially L-shaped cross sectional configuration, one handle having a bottom leg lying in a first plane and a side leg extending from one side edge of said bottom leg, the other handle having a top leg lying in a second plane parallel to said first plane and a side leg extending from a side edge of said top leg, said side legs opposing each other, said coupling means being disposed on said bottom and top legs for nestingly interconnecting said handles and providing a lap joint therebetween.

11. A dental impression tray as in claim 10, wherein said coupling means includes recesses provided in at least one of said bottom and top legs, and associated projections provided on at least the other of said bottom and top legs so as to snap fit said handle sections together.

12. A dental impression tray as in claim 10, wherein the upstanding side walls of one of said half sections are shorter than the upstanding side walls of the other half section.

13. A dental impression tray as in claim 1, wherein said tray includes a tray holder and opposing arcuate half sections, each section having a base wall and upstanding side walls to define said trough, and coupling means for selectively coupling each half section to said tray holder.

14. A dental impression tray as in claim 13, wherein the upstanding side walls of one of said half sections are shorter than the upstanding side walls of the other half section.

15. A dental impression tray as in claim 13, wherein said tray holder includes a flat plate having a substantially arcuate shaped section and an elongated rearwardly extending handle section, said coupling means including raised projections and mating recesses provided between said arcuate shaped section of said tray holder and said base walls of said arcuate half sections.

16. A method for forming a dental prosthesis in situ, comprising:
  (a) forming a negative impression in a dental impression tray of a dental area to be restored, and removing the dental impression tray thereafter;
  (b) performing tooth preparatory work in the dental area to be restored, including removal of portions thereof;
  (c) repositioning the dental impression tray having the negative impression therein onto the dental area so as to form a mold cavity between the negative impression in the tray and the prepared dental area;
  (d) injecting dental restorative material into the mold cavity thus formed so as to form the dental prosthesis, and
  (e) removing the dental impression tray leaving the dental prosthesis in the mouth.

17. A method as in claim 16, and further comprising the step of forming a sprue channel as part of the negative impression in the tray, and utilizing the sprue channel for injection of the dental restorative material.

18. A method as in claim 16, and further comprising the step of forming on an opposing side of a dental impression tray a shallow negative impression of the dental area opposing the dental area to be restored, so as to facilitate the repositioning of the tray into the patient's mouth.

19. A method as in claim 16, and further comprising the step of placing a dental splint in the prepared dental area before the repositioning of the tray so that the dental prosthesis formed will be reinforced by the dental splint being disposed therein.

20. A method as in claim 16, and further comprising the step of coating the negative impression formed in the tray with coloring material so that the dental prosthesis formed will be colored in realistic dental tones to match the remaining dental area.

21. A method as in claim 16, and further comprising the step of inserting a valve in the tray before the formation of the negative impression, placing a shaft through the valve and extending it to the dental area so as to form a sprue channel extending from the valve to the dental area, removing the shaft, and using the valve and sprue channel for injecting the dental restorative material into the mold cavity.

* * * * *